United States Patent [19]

Schenk

[11] Patent Number: 5,126,241
[45] Date of Patent: Jun. 30, 1992

[54] PROCESS FOR THE DETERMINATION OF A SPECIFICALLY BINDABLE SUBSTANCE

[75] Inventor: Roland Schenk, Weilheim, Fed. Rep. of Germany

[73] Assignee: Boehringer Mannheim GmbH, Mannheim-Waldhof, Fed. Rep. of Germany

[21] Appl. No.: 418,516

[22] Filed: Oct. 10, 1989

[30] Foreign Application Priority Data

Oct. 12, 1988 [DE] Fed. Rep. of Germany ....... 3834766

[51] Int. Cl.$^5$ .............. G01N 33/53; G01N 33/542; G01N 33/543
[52] U.S. Cl. ............................... 435/7.1; 435/7.5; 435/7.9; 435/7.92; 435/7.93; 436/501; 436/504; 436/512; 436/518; 436/536; 436/538
[58] Field of Search ............... 435/7.1, 7.9, 975, 7.92, 435/7.93, 7.5; 436/501, 504, 512, 518, 536, 538

[56] References Cited

U.S. PATENT DOCUMENTS

Re. 32,696  6/1988  Schuurs et al. ..................... 435/7
4,945,042   7/1990  Geiger et al. ..................... 435/7.5

FOREIGN PATENT DOCUMENTS 2084317  4/1982  United Kingdom .

Primary Examiner—Esther L. Kepplinger
Assistant Examiner—Toni Scheiner
Attorney, Agent, or Firm—Felfe & Lynch

[57] ABSTRACT

The present invention provides a process for the determination of a specifically bindable substance by incubation of a sample solution with at least three receptors $R_1$, $R_2$ and $R_3$, of which $R_1$ is specifically bindable with $R_2$ and $R_3$, as well as with the substance to be determined, $R_2$ brings about the binding to a solid phase and $R_3$ carries a labelling, separation of bound labelling from unbound labelling and measurement of the labelling in one of the two phases, wherein, as receptor $R_1$, a receptor is used which has at least two binding positions which bind specifically with an epitope of the substance to be determined, as $R_2$ a conjugate of a partner $P_1$ of a specifically binding pair and of a substance S which corresponds to the substance to be determined or is a derivative thereof and has at least one epitope of the substance to be determined, the partner $P_1$ thereby either being bound to a solid phase or being immobilized, and as $R_3$ a complex is used which contains at least the substance S and a labelling.

18 Claims, 4 Drawing Sheets

PROCESS FOR THE DETERMINATION OF A SPECIFICALLY BINDABLE SUBSTANCE

The present invention is concerned with a process for the determination of a specifically bindable substance by incubation of a sample solution with at least three receptors $R_1$, $R_2$ and $R_3$, of which $R_1$ is specifically bindable with $R_2$ and $R_3$, as well as with the substance to be determined, $R_2$ brings about the binding to the solid phase and $R_3$ carries a labelling, separation of bound and unbound labelling and measurement of the labelling in one of the two phases. The present invention also provides a reagent for carrying out this process.

Very many substances occur in body fluids and tissues which are immunologically active, i.e. they are bindable with a specific binding partner and serve as parameters for certain diseases or for the state of health of the human body. These include, inter alia, haptens, for example hormones, proteins, such as tumour labels, protein hormones and viral proteins, as well as antibodies. For the supervision of a medical treatment, the determination of the medicaments in the blood is frequently also necessary. Examples therefor include anti-epileptics, antibiotics, digitalis and opiates. Since these substances often only occur in very small amounts, processes according to the immunoassay principle are used for the detection thereof. There are many variants of this. The different immunological processes of determination can be divided into homogeneous and heterogeneous processes. In the case of heterogeneous processes, a solid phase reaction always participates in order to be able to separate the bound part of the labelled components from the unbound ones. In the case of the homogeneous process variant, no separation of bound labelling and unbound labelling takes place so that a differentiation of bound and unbound labelling must take place by other methods.

For carrying out heterogeneous immunoassays, there are essentially two variants in which, on the one hand, an antibody against the substance to be determined is immobilised and, on the other hand, the substance to be determined is itself immobilised. In the first variant, a sample solution which contains the substance to be determined and a conjugate of the substance to be determined and a labelling are incubated with an immobilised antibody, the substance to be determined and the labelled substance thereby competing for the binding to the antibody. The more substance to be determined is present in the solution, the less labelled substance can be bound. Therefore, the amount of labelled substance is an indirect measure for the amount of substance to be determined. After separation of solid and liquid phase, the labelling can be determined in one of the two phases.

In another variant, the sample solution which contains the substance to be determined is incubated with a labelled antibody specific for it, as well as the immobilised sample substance, immobilised sample substance and the substance to be determined present in the solution thereby competing for the binding to the antibody. The more substance to be determined is present in the solution, the less labelled antibody is bound by binding to the immobilised sample substance on the solid phase. The amount of bound labelled antibody is thus also an indirect measure for the amount of substance to be determined in the sample solution. Here, too, after separation of the solid phase from the liquid phase, the amount of bound labelling is determined.

It is a disadvantage of these processes that modified antibodies must always be used. In the first case, the antibody is bound to a solid phase and, in the second case, the antibody is bound to a labelling substance. This modification is laborious and can lead to undesired changes of the properties of the antibody, for example a reduction of the specificity and affinity. This is the reason why polyclonal antibodies often cannot be used but rather, with great expense, there must be used monoclonal antibodies selected for low cross-reactivity and high affinity which, in addition, must mostly be purified in a laborious manner. Furthermore, for each individual determination, all reagents must be specifically selected, which is also unfavourable. Admittedly it is already known from Federal Republic of Germany Patent Specification No. 31 38 489 to carry out the immobilisation of formed labelling complexes without the participation of antibodies but also in the case of this process a labelled and thus modified antibody is necessary.

Therefore, it is an object of the present invention to provide a process for the determination of immunologically active substances which can be widely used, in which antibodies can be employed without modification and in which it is not absolutely necessary to use monoclonal antibodies.

Thus, according to the present invention, there is provided a process for the determination of a specifically bindable substance by incubation with three receptors $R_1$, $R_2$ and $R_3$, of which $R_3$ is specifically bindable with $R_1$ and $R_2$, as well as with the substance to be determined, $R_2$ brings about the binding to a solid phase and $R_3$ carries a labelling, separation of bound labelling from unbound labelling and measurement of the labelling in one of the two phases, wherein, as receptor $R_1$, there is used a receptor which has at least two binding positions which bind specifically with an epitope of the substance to be determined, $R_2$ is a conjugate of a partner $P_1$ of a specifically binding pair and of a substance S which corresponds to the substance to be determined or is a derivative thereof and has at least one epitope of the substance to be determined, the partner $P_1$ thereby either being bound to a solid phase or being immobilised, and as $R_3$ there is used a complex which contains at least the substance S and a labelling.

The process according to the present invention can be used for the determination of practically all substances which are to be determined in body fluids or tissue extracts and are capable of a specific binding. Substances present in low concentration can be detected just as well as substances present in high concentration. The present invention provides the possibility of being able to carry out determinations quickly and dependably with simple reagents.

The process is especially useful for the determination of haptens, i.e. substances which possess only one binding position for a specifically bindable partner. As examples therefor, there can be mentioned hormones and medicaments, such as anti-epileptics, antibiotics, digitalis and opiates.

Surprisingly, we have found that, in the case of carrying out the process according to the present invention, in contradistinction to the known processes, high demands do not have to be made on the quality of the antibodies so that polyclonal antibodies can here readily be used. Furthermore, we have ascertained that the blank values obtained are very low and thus the sensitivity is increased in comparison with known processes.

By epitope in the description of the present invention, there is to be understood a binding position which can enter into a specific binding with another substance. Examples of epitopes are antigenic determinants on antigens and haptens and also specific binding positions on proteins.

Figure 1:
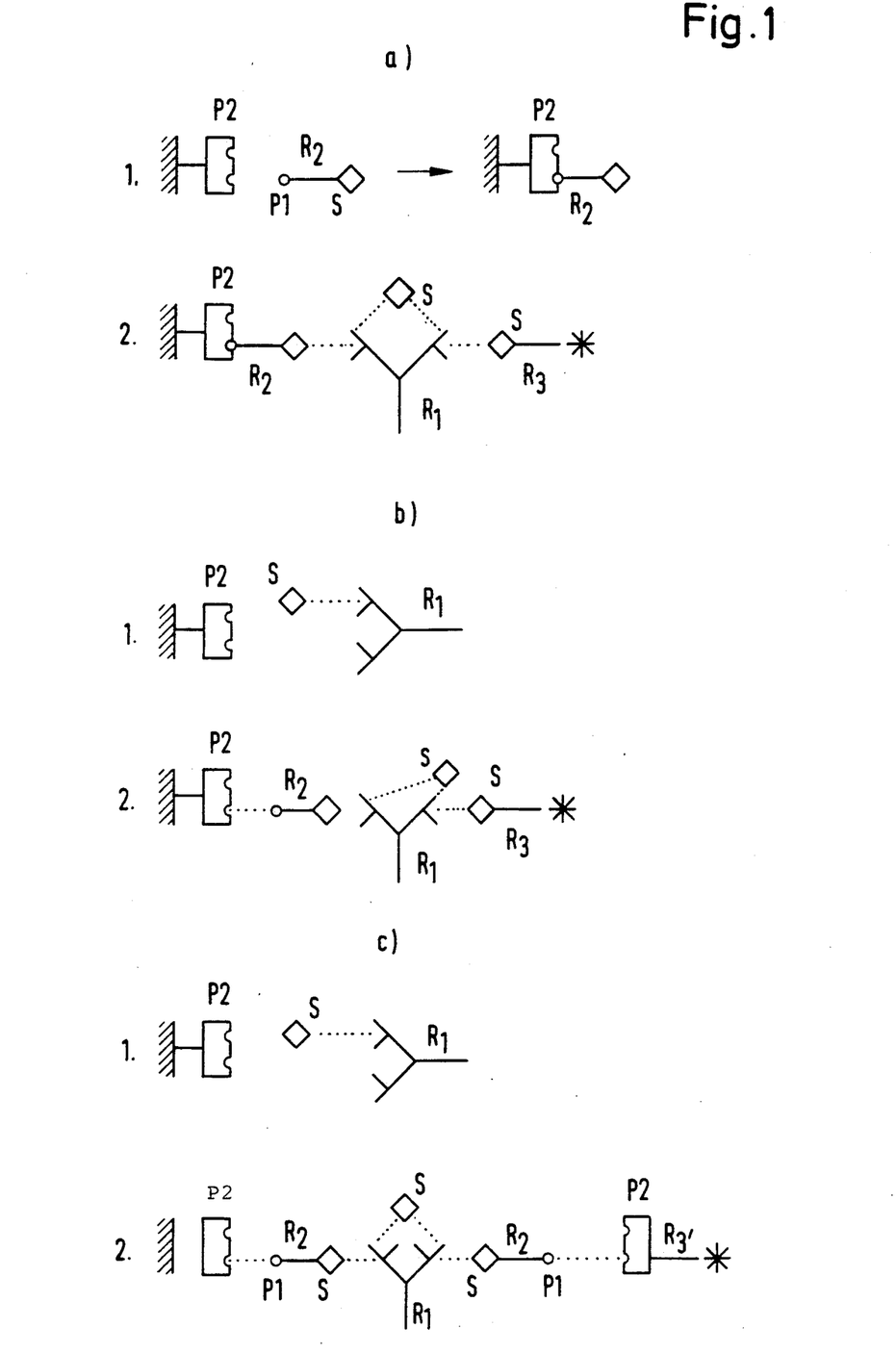
FIG. 1 shows three reaction schemes for preferred embodiments of the process according to the present invention.

For carrying out the process according to the present invention, the sample solution is incubated with three receptors $R_1$, $R_2$ and $R_3$. Receptor $R_2$ is specifically bindable with the receptors $R_2$ and $R_3$, as well as with the substance to be determined, and carries a labelling. Receptor $R_2$ brings about the binding to the solid phase. Various reaction principles which can be carried out with the process according to the present invention are illustrated in FIG. 1 of the accompanying drawings. A preferred process variant is thereby that indicated with 1$a$). In this case, into a reaction vessel, to the walls of which are bound a plurality of partners $P_2$ of a specifically binding pair complementary to $P_1$, there is added receptor $R_2$ which is a conjugate of the substance S and the partner $P_1$ of the specifically binding pair. The conjugate binds via partner $P_1$ to partner $P_2$. Subsequently, there is added to the reaction vessel receptor $R_1$ which has at least two binding positions for an epitope of the substance to be determined and $R_3$ which is a conjugate of the substance S and a labelling. In the solution, the part S of $R_2$, the part S of $R_3$ and the substance to be determined then compete for the binding to receptor $R_1$. If $R_1$ is, for example, a bivalent antibody, then the following complexes are formed:

$R_1$ to the two paratopes of which is bound $R_2$ via S $R_1$ to the two paratopes of which is bound the substance to be determined $R_1$ to the two paratopes of which is bound $R_3$ via S, as well as mixed complexes, namely:

$R_1$ to one paratope of which is bound the substance to be determined and to the other paratope of which is bound $R_3$ or $R_2$ via S and $R_1$ to one paratope of which is bound $R_3$ via S and to the other paratope of which is bound $R_2$ via S.

Only the complexes which are bound to $R_2$ are immobilised and only the complexes in which a receptor $R_3$ is bound can be evaluated via the determination of the bound labelling. The more of the substance to be determined is contained in the solution, the less $R_2$ and $R_3$ are bound to $R_1$ and the less complexes are thus immobilised or carry a labelling. Thus, the proportion of bound labelling is an indirect measure for the substance to be determined and can be evaluated via a calibration curve.

The process of carrying out by variant b) serves for the detection of substances which are present in the sample solution in very low concentrations. Here, in the first step, the matrix to which are bound the partners $P_2$ of the specifically binding pair is incubated with the substance to be determined, as well as receptor $R_1$. The substance to be determined present in the sample solution can thereby bind with receptor $R_1$. A binding to the solid phase cannot take place. In a second step, receptors $R_2$ and $R_3$ are then added thereto. The added receptors then compete for the binding to receptor $R_1$ to which the substance to be determined is already partly bound. The more of the substance to be determined is already bound, the less receptors $R_2$ and $R_1$ can be bound. Since receptor $R_2$ also contains partner $P_1$ which is bindable with partner $P_2$ of the matrix, it results in the immobilisation of the complexes being formed. The evaluation again takes place after separation of bound phase from liquid phase by evaluation of the labelling, which takes place via a calibration curve.

Variant c) shows a form of carrying out in which the matrix forming the solid phase and the labelling conjugate can remain the same for all determinations. Here again, in a first step, the matrix, which carries the partner $P_2$ of the specific binding pair, is incubated with the substance to be determined and receptor $R_1$, whereby the substance to be determined can bind to receptor $R_1$. In the second step, there are then simultaneously added thereto the conjugate $R_2$ of the substance to be determined and partner $P_1$ and a conjugate $R_3'$ of partner $P_2$ and a labelling. The conjugate $R_2$ of substance to be determined and partner $P_1$, as well as the substance to be determined from the sample solution, then compete for the binding to receptor $R_1$. Furthermore, the partner $P_2$ bound to the matrix, as well as the conjugate $R_3'$ of partner $P_2$ and labelling, compete for the binding to one of the partners $P_1$. Here, too, there again takes place an evaluation of the bound labelled complexes via a calibration curve.

In the case of this variant, the concentrations of $R_1$, thus especially of the antibody, and of $R_2$ are adapted to the sample concentration in the test. The conjugate of partner $P_2$ and a labelling should thereby be used in an amount which binds not more than about one half of the conjugate $R_2$ of the substance to be determined and $P_1$ in order that of the latter conjugate sufficient is available for the binding to the matrix-bound partner $P_2$, which should be present in excess. The conjugate $R_2$ containing $P_1$ is advantageously used in an amount which lies in the order of magnitude of the substance to be determined, thus about $10^{-5}$ mole/liter (e.g. in the case of theophylline) to $10^{-10}$ mole/liter (e.g. in the case of digoxin). In the case of variant c), $R_2$ should have only one binding position for $P_2$ (on the matrix or in the conjugate) in order to avoid a disturbance of the cross-linking. This does not apply to variants a) and b).

This embodiment has, on the one hand, the great advantage that only a single specific conjugate—the conjugate of S and $P_1$—must be made available and, on the other hand, the immunological reaction takes place homogeneously, which distinctly increases the sensitivity and reproducability.

Thus, for the process principle defined according to the present invention, there are many variants of carrying it out. In every case, at least three receptors are necessary.

The substance to be determined can be any substance capable of a specific binding and, especially as defined above, can be a hapten.

As first receptor $R_1$, there is used a receptor which has at least two binding positions which bind specifically with an epitope of the substance to be determined. This receptor is selected depending upon the particular substance to be determined. There is here preferred a monoclonal or polyclonal antibody or the Fab$_2$ fragment thereof.

Receptor $R_2$ is a conjugate of a partner of a specifically binding pair $P_1$ and a substance S which corresponds to the substance to be determined or is a derivative thereof and has at least one epitope of the substance to be determined. Pairs which are specifically bindable with one another are known. Appropriate binding pairs ($P_1$-$P_2$) are, in particular, biotin-streptavidin or avidin; hapten-antibody; antigen-antibody; concanavalin-antibody; sugar-lecithin; hapten-binding protein, for example thyroxine-binding globulin and thyroxine or oligopeptide-antibody.

As binding pair, there is especially preferably used biotin and streptavidin or avidin so that receptor $R_2$ especially preferably contains biotin as partner $P_1$.

The part S of the receptor $R_2$ can preferably correspond to the unchanged substance to be determined. However, it can also be a derivative of the substance to be determined, for example a protein epitope. The only thing which is important is that the part S is bindable with receptor $R_1$, whereby it is not absolutely necessary that S and the substance to be determined bind with the same binding strength to $R_1$.

The preparation of the conjugates takes place in known manner, for example analogously to the description given in Eur. J. Biochem., 131, 333-338/1980.

Receptor $R_2$ brings about the binding to the solid phase. $R_2$ can, in one variant, be bound directly or via a spacer to a solid phase via $P_1$. In another variant, the binding to the solid phase takes place during the immunological reaction by the binding of $P_1$ to the partner $P_2$ of the specifically binding pair immobilised on the solid phase.

In a further preferred embodiment of the process, a receptor $R_2$ is used which is a conjugate of S and $P_1$. As solid phase, a matrix is used on which is also immobilised a plurality of partners $P_1$ of the specifically bind pair. After incubation of the components necessary for the immunological reaction, there is then added partner $P_2$ which has at least two binding positions for $P_1$. In this way, there then takes place the immobilisation of the receptors $R_2$.

As solid phase, there are especially preferred reagent glasses or microtitre plates of polystyrene and similar synthetic resins which are adsorptively coated on the inner surface with $P_1$ or $P_2$. There are also suitable particulate substances, for example molecular sieve materials, glass pearls, synthetic resin tubes and the like. As solid phase, there are also suitable porous, laminar carriers, for example paper. Also preferred is an embodiment in which the solid phase consists of magnetic particles such as are described, for example, in European Patent Specification No. 0,240,770 and in U.S. Pat. Nos. 4,141,687 and 4,197,337. The magnetic particles preferably consist of chromium dioxide and iron oxide. The binding of the partner $P_2$ to the particles can take place, for example, in the manner described in European Patent Specification No. 0,240,770.

Receptor $R_3$ is a complex which contains at least the substance S and a labelling. As labelling, there is thereby used an enzyme or a fluorescing, chemiluminescing or radio-active substance. Processes for labelling are well known, for example from Clin. Chim. Acta, 81, 1-40 /1977, and do not here require any further explanation. The labelling can be determined in known manner.

Receptor $R_3$ can also first be formed during the immunological reaction from a conjugate which contains the substance S and a partner $P_1$ of a specifically-binding pair and a conjugate of the partner $P_2$ of the specifically-binding pair and a labelling.

The process can be carried out in one or more steps. The evaluation takes place in known manner. Since each of the receptors and also the substance to be determined can, in each case, only react specifically with the reaction partner intended for it, it is possible to incubate together all receptors and the sample and to carry out the process in one step. This is especially advantageous in the case of carrying out the process in an automatic analyser.

For the detection of substances of very low or very high concentration, multi-step process variants are preferred.

The carrying out of all process variants preferably takes place in a buffered solution. Buffer systems for these processes are known. For this purpose, there are especially preferred GOOD buffer and phosphate buffer.

According to the present invention, there is provided a process which can be carried out simply and quickly and which is very sensitive also in the case of using polyclonal antibodies.

The present invention also provides a reagent for the determination of specifically-bindable substances which contains receptor $R_1$, which has at least two binding positions specific for the substance to be determined, receptor $R_2$, which is a conjugate of a partner $P_1$ of a specifically-binding pair and of a substance S, which corresponds to the substance to be determined or is a derivative thereof, and receptor $R_3$, which is a complex which contains at least a partner $P_1$ and the substance S, and physically separated therefrom a solid phase.

In a further embodiment, the reagent according to the present invention contains a solid phase to which are bound a plurality of partners $P_2$ of a specifically-binding pair, as well as, physically separated therefrom, the receptors $R_1$, $R_2$ and $R_3$ or $R_3'$.

In a further embodiment, the reagent according to the invention contains a solid phase to which are bound the partners $P_1$, and, physically separated therefrom, partners $P_2$ of the specifically-binding pair and receptors $R_1$ $R_2$ and $R_3$ or $R_3'$.

In a further preferred embodiment there is used a multilayer reagent combination which, in a first layer contains the solid phase with partner $P_2$ and receptor $R_3'$ and physically seperated from said first layer receptors $R_1$ and $R_2$.

In a further embodiment, there is used a reagent combination which, in a first reagent, contains a suspension of the magnetic particles coated with partner $P_2$ and a solution of the receptor $R_3'$ (reaction scheme 1c), and physically separated therefrom the receptors $R_1$ and $R_2$. As specifically-binding pair for $P_1/P_2$, there is preferably used biotin/avidin or streptavidin.

This reagent is suitable for the determination of a plurality of parameters in body fluids and tissue extracts.

In a preferred embodiment, the reagent additionally contains buffer substances. Especially preferably, it contains phosphate buffer or GOOD buffer.

The present invention will now be described in more detail with reference to the following Examples and the accompanying drawings, in which.

In FIG. 1 are shown schemes for the reaction principles of various preferred embodiments of the process according to the present invention. In all of the variants shown, receptor $R_1$ is an antibody.

FIG. 1a shows a variant in which first a solid phase to which are bound the partners $P_2$ of a specifically-binding pair is incubated with receptor $R_2$, the partner $P_1$ of the specifically-binding pair, a solid phase thereby resulting to which receptors $R_2$ are bound via $P_1$. In a second step, this solid phase is then incubated with receptors $R_1$, $R_3$ and the sample solution.

Variant 1b shows an embodiment in which, in a first step, a solid phase to which are bound the partners $P_2$ is incubated with receptor $R_2$ and the sample solution. In a second step, receptors $R_1$ and $R_2$ are added thereto.

Variant 1c shows an embodiment in which a solid phase, to which are bound partners $P_2$, and conjugates of labelling and partner $P_2$ are used which, in each case, are independent of the substance to be determined. The receptors $R_1$, $R_2$ and $R_3$, as well as the sample, are incubated with the solid phase and labelling conjugate.

EXAMPLE 1

Determination of $T_4$ According to Reaction Scheme 1a)

Figure 2:
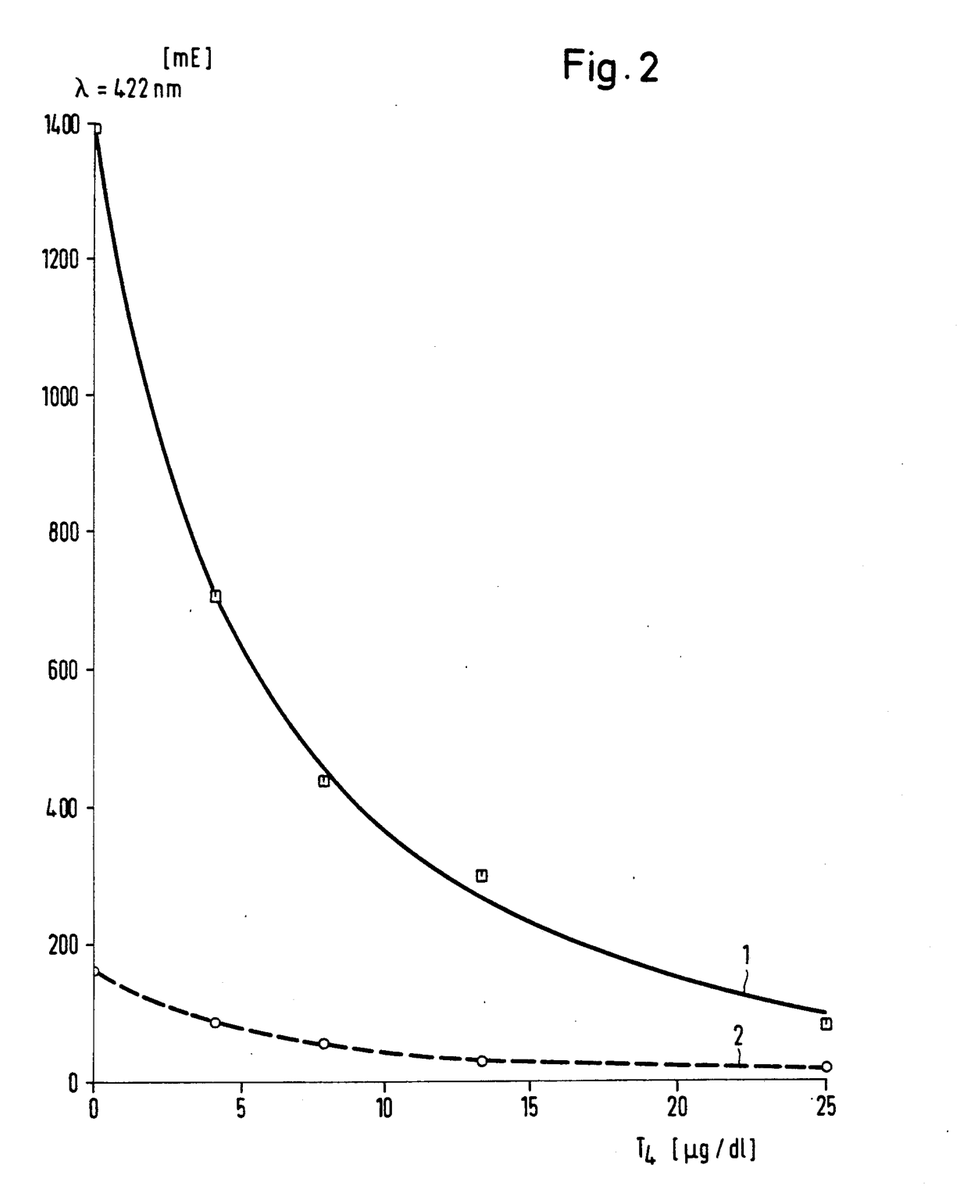
FIG. 2 shows a calibration curve for a $T_4$ determination with the use of $T_4$-POD conjugate (reaction scheme 1a). Curve 1: 10 nmole/liter $T_4$-biotin; curve 2: 1 nmole/liter $T_4$-biotin (end concentration in the test).

Buffer A:
120 mmole/liter barbiturate
18.2 mmole/liter phosphate buffer (pH 8.6)
1.27 mmole/liter 8-anilino-1-naphthalenesulphonic acid
0.2% by weight bovine serum albumin 980 μl. of buffer A and 20 μl. of a solution of a conjugate of $T_4$ and biotin (preparation according to Example 4 (end concentration 1 or 10 mmole/ml.)) are introduced into a streptavidin-coated polystyrene vessel (produced according to European Patent Specification No. 0,269,092) and incubated for 30 minutes at 25° C. Subsequently, the vessel is washed and 50 μl. of sample (human serum made up with $T_4$), 980 μl. of buffer A, 20 μl. of a solution of 0.1 mg./ml. polyclonal antibody against $T_4$ and 2.5 U/ml. $T_4$-peroxidase conjugate (5 mU/test) added thereto, incubated for 30 minutes at 25° C., washed and 1 ml. of a solution of 9.1 mmole/liter ABTS ® (2,2'-azino-di-(3-ethylbenzthiazoline-6-sulphonic acid diammonium salt) added thereto. After a further incubation for 30 minutes at 25° C., the optical density is determined at 422 nm as a measure for the $T_4$ content. The results are given in FIG. 2 of the accompanying drawings.

EXAMPLE 2

Determination of $T_4$ According to Reaction Scheme 1b)

Figure 3:
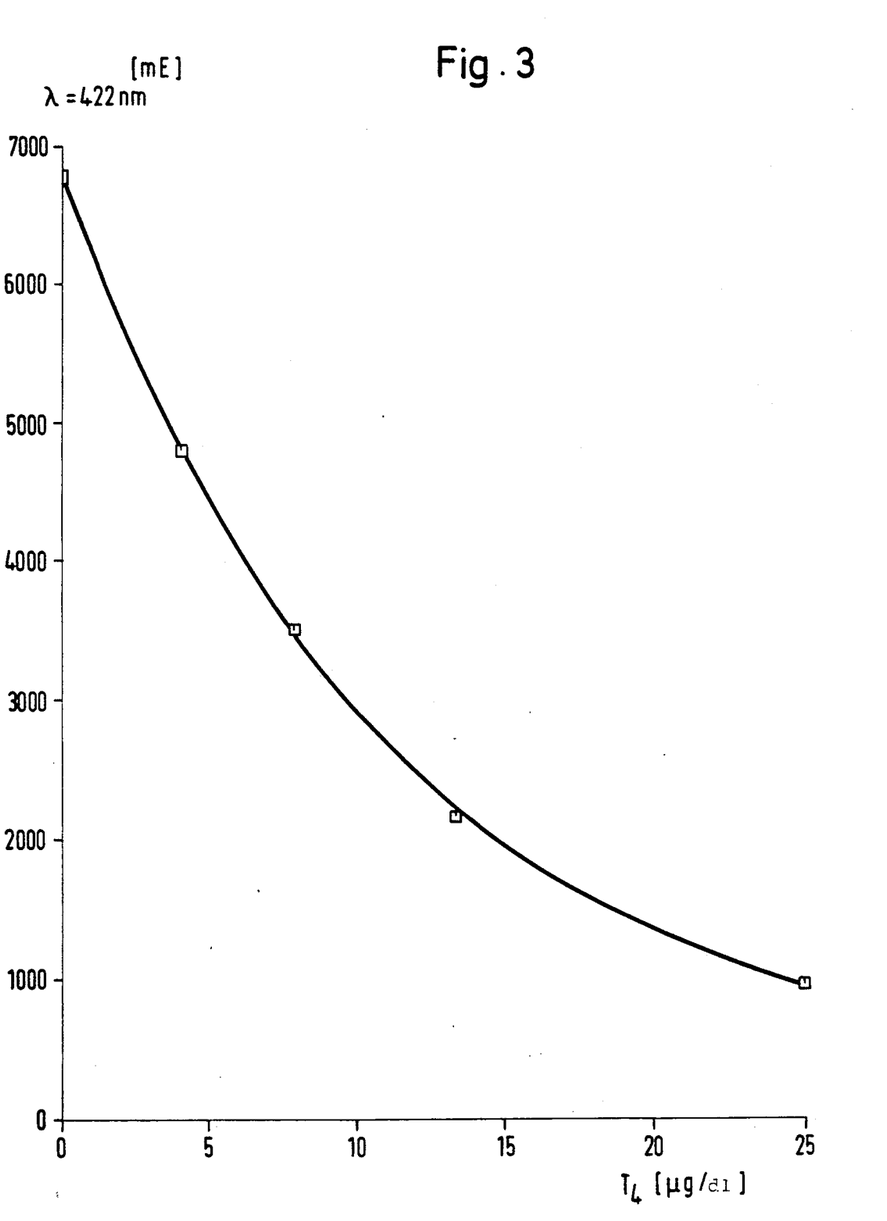
FIG. 3 shows a calibration curve for a $T_4$ determination with the use of a $T_4$-POD conjugate (reaction scheme 1b)

50 μl, of sample (human serum made up with $T_4$) are incubated with 480 μl. of buffer A and 20 μl. of a solution of a polyclonal antibody against $T_4$ (0.1 mg./ml.) at 25° C. for 30 minutes in a polystyrene vessel coated with streptavidin. Subsequently, 480 μl. of buffer A and 20 μl. of a solution of $T_4$-biotin conjugate ($5 \times 10^{-8}$ mole/liter, corresponding to 1 nmole/liter end concentration in the test) and $T_4$-POD conjugated (2.5 U/ml., 50 mU/test) are added thereto and incubated for 30 minutes at 25° C. The vessel is washed and subsequently 1 ml. ABTS ® solution (9.1 mmole/liter) added thereto, incubated for 30 minutes at 25° C. and subsequently the optical density is determined at 422 nm as a measure for the $T_4$ content. The results are given in FIG. 3 of the accompanying drawings.

EXAMPLE 3

Determination of $T_4$ According to Reaction Scheme 1c

Figure 4:
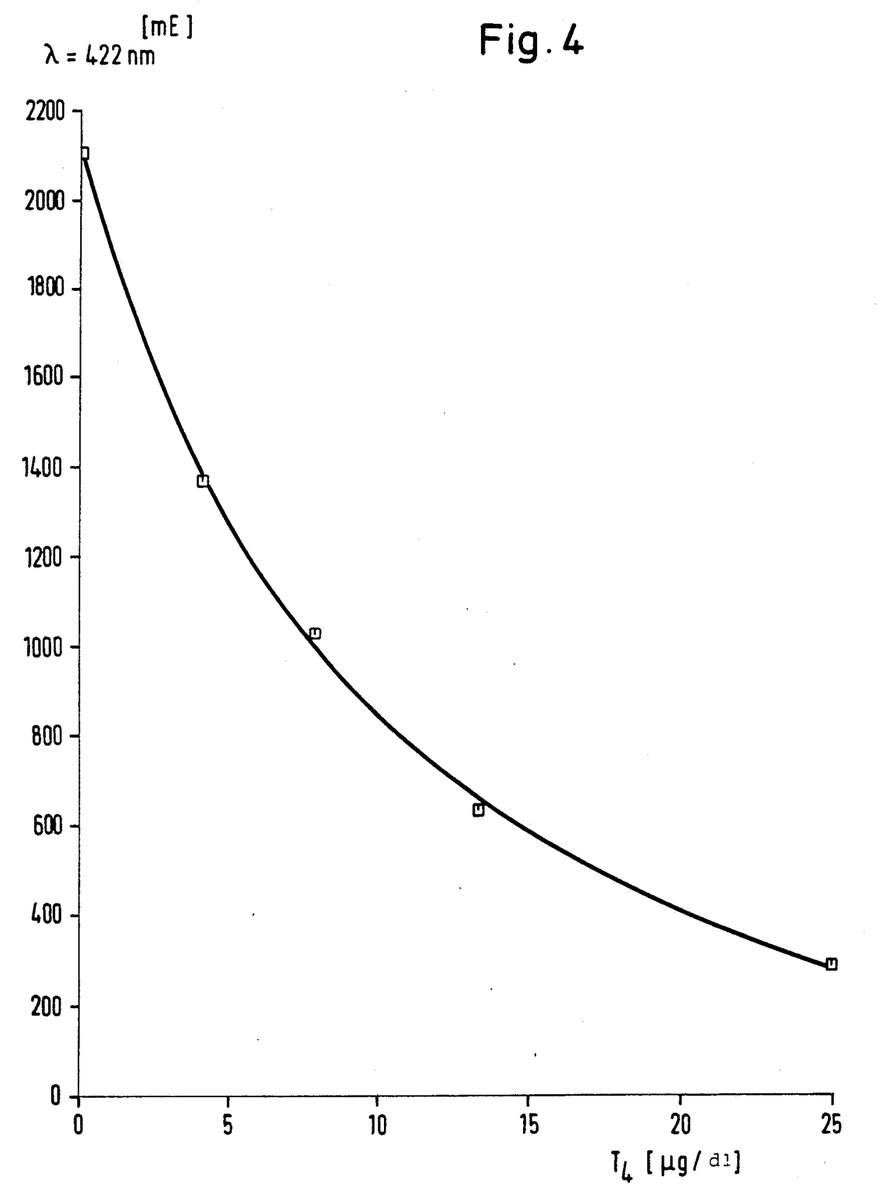
FIG. 4 shows a calibration curve for a $T_4$ determination with the use of a $T_4$-biotin conjugate and of a streptavidin-POD conjugate (reaction scheme 1c).

50 μl. of sample (human serum made up with $T_4$) are incubated with 480 μl. of buffer A and 20 μl. of a solution of a polyclonal antibody against $T_4$ (0.1 mg./ml.) for 30 minutes at 25° C. in a polystyrene vessel coated with streptavidin. Subsequently, 480 μl. of buffer A and 20 μl. of a solution of a conjugate of $T_4$-biotin ($5 \times 10^{-7}$ mole/liter, corresponding to 10 nmole/liter end concentration in the test) and 2.5 U/ml. streptavidin-POD conjugate (50 mU/test) are added thereto and incubated for 30 minutes at 25° C. The vessel is washed and 1 ml. ABTS ® solution (9.1 mmole/liter) added thereto, incubated at 25° C. for 30 minutes and the optical density determined at 422 nm as a measure of the $T_4$ content. The results are given in FIG. 4 of the accompanying drawings.

EXAMPLE 4

Preparation of $T_4$-Biotin Conjugate

N-tert.-butoxycarbonyltetraiodothyronine is coupled via pentamethylenediamine with biotin in the manner described in Eur. J. Biochem., 131, 333-338/1980.

I claim:

1. Method for determination of a specifically bindable substance comprising:
   incubating a liquid sample with at least three receptors $R_1$, $R_2$ and $R_3$, wherein
   (a) $R_1$ specifically binds with $R_2$, $R_3$ and said specifically bindable substance and is an antibody or an Fab$_2$ fragment;
   (b) $R_2$ comprises a conjugate of (i) a substance S which is identical to the specifically bindable substance to be determined and (ii) a first partner $P_1$ of a binding pair,
   (c) $R_3$ comprises a conjugate of S and a label, to form complexes containing $R_1$, $R_2$ and $R_3$,
   (d) adding a second partner of a specific binding pair $P_2$ to said liquid sample together with a solid phase, wherein $P_2$ binds to said solid phase and to $P_1$ to immobilize said complexes containing $R_1$, $R_2$ and $R_3$, and,
   determining $R_3$ bound to solid phase or in liquid phase as a determination of said specifically bindable substance.

2. Method for determination of a specifically bindable substance, comprising:
   incubating a liquid sample with at least three receptors $R_1$, $R_2$ and $R_3$, and with a solid phase bound partner $P_2$ of a binding pair, wherein:
   a) $R_1$ specifically binds with $R_2$, $R_3$ and said specifically bindable substance and is an antibody or an Fab$_2$ fragment;
   (b) $R_2$ comprises a conjugate of (i) a substance S which is identical to the specifically bindable substance to be determined and (ii) a first partner $P_1$ of a binding pair;
   (c) $R_3$ comprises a conjugate of S and a label.
   (d) $P_2$ binds to $P_1$, to form immobilized complexes containing $R_1$, $R_2$ and $R_3$. and;
   determining $R_3$ bound to solid phase or in liquid phase as a determination of said specifically bindable substance.

3. Method of claim 2, wherein $P_2$ is bound to said solid phase via solid phase bound $P_1$.

4. Method of claim 2, comprising adding said solid phase bound member of a specific binding pair $P_2$ after addition of $R_1$, $R_2$ and $R_3$ to said sample solution.

5. Method of claim 1, wherein $P_1$ is biotin and $P_2$ is streptavidin, avidin or a biotin specific antibody.

6. Method of claim 2, wherein $P_1$ is biotin and $P_2$ is streptavidin, avidin or a biotin specific antibody.

7. Method of claim 1, wherein $R_3$ consists of S and a label.

8. Method of claim 2, wherein $R_3$ consists of S and a label.

9. Method of claim 1, wherein said label is radioactive chemiluminescent, or fluorescent.

10. Method of claim 2, wherein said label is radioactive chemiluminescent, or fluorescent.

11. Method of claim 1, wherein $R_3$ comprises a first member complex consisting of S and $P_1$ and a second member complex consisting of $P_2$ and a label, wherein $P_1$ and $P_2$ are bound to each other.

12. Method of claim 2, wherein $R_3$ comprises a first member complex consisting of S and $P_1$ and a second member complex consisting of $P_2$ and a label, wherein $P_1$ and $P_2$ are bound to each other.

13. Method of claim 1, wherein $P_1$ and $P_2$ are selected from the group consisting of biotin-streptavidin, biotin-avidin, biotin-biotin specific antibody, antigen-antigen specific antibody, hapten-hapten binding protein and oligopeptide-oligopeptide specific antibody.

14. Method of claim 2, wherein $P_1$ and $P_2$ are selected from the group consisting of biotin-streptavidin, biotin-avidin, biotin-biotin specific antibody, antigen-antigen specific antibody, hapten-hapten binding protein and oligopeptide-oligopeptide specific antibody.

15. Method of claim 1, wherein said solid phase is a matrix consisting of a synthetic resin and $P_2$ is bound thereto via a spacer.

16. Method of claim 2, wherein said solid phase is a matrix consisting of a synthetic resin and $P_2$ is bound thereto via a spacer.

17. Method of claim 1, wherein $P_1$ is biotin and $P_2$ is avidin or streptavidin.

18. Method of claim 2, wherein $P_1$ is biotin and $P_2$ is avidin or streptavidin.

* * * * *

UNITED STATES PATENT AND TRADEMARK OFFICE
CERTIFICATE OF CORRECTION

PATENT NO. : 5,126,241
DATED : June 30, 1992
INVENTOR(S) : Roland Schenk It is certified that error appears in the above-identified patent and that said Letters Patent is hereby corrected as shown below:

Column 3, line 11: change second "$R_2$" to -- $R_1$ --.

Signed and Sealed this

Thirtieth Day of November, 1993

Attest:

BRUCE LEHMAN

*Attesting Officer*     *Commissioner of Patents and Trademarks*